United States Patent [19]

Aoyagi et al.

[11] Patent Number: 4,836,928
[45] Date of Patent: Jun. 6, 1989

[54] SEPARATION METHOD, SEPARATION DEVICE AND SEPARATION APPARATUS FOR SEPARATING BODY FLUID INTO RESPECTIVE COMPONENTS

[75] Inventors: Juuro Aoyagi, Tokyo; Yuichi Yamamoto, Fujinomiya; Toshihiro Akaike, Hoya; Yasuhiro Nozaki, Ootsu, all of Japan

[73] Assignee: Terumo Kabushiki Kaisha, Tokyo, Japan

[21] Appl. No.: 727,905

[22] Filed: Apr. 26, 1985

[30] Foreign Application Priority Data

Apr. 28, 1984 [JP] Japan .................. 59-86569

[51] Int. Cl.⁴ .................. B01D 13/01; B01D 15/08
[52] U.S. Cl. .................. 210/635; 210/198.2; 210/321.87; 210/490; 210/656; 435/2; 436/178
[58] Field of Search .................. 210/198.2, 635, 656, 210/745, 490, 927, 500.1, 500.2, 506, 321.87, 321.88, 321.89, 321.9; 435/2, 30, 241, 803; 422/101; 436/177, 178

[56] References Cited

U.S. PATENT DOCUMENTS

| | | | |
|---|---|---|---|
| 3,593,855 | 7/1971 | Stana | 210/500.2 |
| 3,780,147 | 12/1973 | Stana | 210/500.2 X |
| 4,124,701 | 11/1978 | Bach et al. | 424/12 |
| 4,234,317 | 11/1980 | Lucas et al. | 422/101 |
| 4,252,653 | 2/1981 | Beck et al. | 210/507 |
| 4,490,216 | 12/1984 | McConnell | 435/817 X |
| 4,572,897 | 2/1986 | Amotz et al. | 435/177 |
| 4,681,582 | 7/1987 | Yamamoto | 604/84 |

FOREIGN PATENT DOCUMENTS

| | | |
|---|---|---|
| 63947 | 4/1981 | European Pat. Off. . |
| 52-114013 | 9/1977 | Japan . |
| 54-122713 | 9/1978 | Japan . |
| 55-149839 | 11/1980 | Japan . |
| 56-135158 | 10/1981 | Japan . |
| 56-151356 | 11/1981 | Japan . |
| 58-170717 | 7/1983 | Japan . |
| 2077137 | 12/1981 | United Kingdom . |

OTHER PUBLICATIONS

Akimoto et al, Polymer Model Membranes, Agnew. Chem. Int. Ed. Engl. 20 (1981) No. 1, pp. 90–91.

Primary Examiner—W. Gary Jones
Attorney, Agent, or Firm—Frishauf, Holtz, Goodman & Woodward

[57] ABSTRACT

A body fluid is separated into respective components by passing the body fluid through a separation device. The separation device includes a lipid having lipophilic and hydrophilic groups, and a support immobilizing the lipid. The lipid is immobilized on the support such that only its hydrophilic groups contact the body fluid introduced in the separation device. Only body fluid components having a strong adherent property adhere to the hydrophilic groups of the lipid.

10 Claims, 3 Drawing Sheets

SEPARATION METHOD, SEPARATION DEVICE AND SEPARATION APPARATUS FOR SEPARATING BODY FLUID INTO RESPECTIVE COMPONENTS

BACKGROUND OF THE INVENTION

1. Field of the Invention

The present invention relates to a separation method, a separation device and a separation apparatus for separating a body fluid such as lymph or blood into respective components and, more particularly, to a separation method, separation device and a separation apparatus for separating a body fluid into its respective components utilizing the difference in adherence of each body fluid component to hydrophilic groups of a lipid.

In a description to follow, the body fluid component is exemplified by lymphocytes and the present invention will be described with respect to separation of limphocytes into its fractions, i.e., T-cells and B-cells. However, the present invention is not limited thereto and can be widely adapted to separation of other body fluid components such as blood components or ascites components.

2. Description of the Prior Art

Lymphocytes play an important role in the immunological surveillance mechanism but are also associated with factors leading to diseases such as the Good syndrome. For this reason, in order to allow analysis of a biological defense mechanism or of interaction between cells or to allow clinical tests of an immunological deficiency syndrome, separation of lymphocytes into T-cells or B-cells or into its subsets having specific functions is an important task.

Cell populations called lymphocytes are known to be classified into at least two types having properties different in various respects. Typically, such cell populations are T-cells, i.e., thymus-derived lymphocytes, and B-cells, i.e., bone marrow-derived lymphocytes.

No conventional separation method of T- and B-cells allows complete separation of lymphocytes into T- and B-cells in one step. According to any conventional method of separating peripheral blood into T- and B-cells, in a first step, a leucocyte supernatant containing 70 to 90% of lymphocytes is separated from leucocytes by centrifugation using a high-density isotonic solution such as Ficoll-Paque, and the supernatant is then subjected to a second step. Six methods are mainly known as methods used in the second step:

(1) The rosette formation method using erythrocytes of sheep treated with neuraminidase (2) The column method using nylon fiber (3) The separation method using a water-insoluble, hydrophobic solid having a porous surface, or, a granular hydrophobic solid having acidic functional groups (4) The separation method using a fluorescence cell sorter (5) The continuous electrophoresis method using no carrier (6) Affinity chromatography However, the above methods have the following problems:

In the method (1), since the erythrocytes of sheep and lymphocytes are caused to exist in common, the lymphocytes are subject to stimulation.

The method (2) does not allow complete separation and cannot provide a satisfactory recovery rate of T-cells. In addition, no method is available for separating B-cells adhering to nylon fiber in a viable state.

Although the method (3) has a good separation effect and a good recovery rate of T-cells, it has only a low recovery rate of B-cells.

Since the method (4) uses an antiserum as a fluorescent label, the cells are subject to stimulation or damage. In addition, the method does not allow separation of a massive amount of lymphocytes such as about $10^7$ to $10^8$ lymphocytes.

The method (5) has an advantage of allowing separation of a massive amount of lymphocytes. However, mobility of cells differs depending upon their maturity, and the influence of the electric field on the cells has not yet been known.

The method (6) involves an unknown factor in respect of a change in functions of cells.

The methods (1) to (6) except for the method (5) commonly suffer from the problem of complex procedures or a long treatment time.

Although practical prior arts are disclosed as per Japanese Patent Disclosure Nos. 56-14088 and 58-74611, they both belong to one of the methods enumerated above and are therefore subject to the same problems.

SUMMARY OF THE INVENTION

The present invention has been made in consideration of the above situation and has as its object to provide a separation method, a separation device and a separation apparatus, which allow effective separation of body fluid components such as T- and B-cells of lymphocytes without impairing their functions with simple steps and without requiring a special apparatus, and which have a wide range of applications including not only clinical tests but also therapy of immunological diseases and culture of cells.

According to a first aspect of the present invention, there is provided a body fluid component separation method wherein body fluid is brought into contact substantially only with hydrophilic groups of a lipid containing lipophilic groups and such hydrophilic groups, and the body fluid components are separated into a body fluid component having a strong adherent property to the hydrophilic groups and into that having a weak adherence thereto utilizing the difference in adherence of body fluid components to the hydrophilic groups.

According to a second aspect of the present invention, there is provided a body fluid component separation device wherein a lipid having lipophilic and hydrophilic groups is immobilized on a carrier such that the hydrophilic groups can be brought into contact with body fluid components to be separated, and body fluid components are separated into respective components utilizing the difference in adherence to the hydrophilic groups.

According to a third aspect of the present invention, there is provided a body fluid component separation apparatus comprising a housing having body fluid inlet and outlet ports communicating with each other through a body fluid flow path, and a body fluid component separation device which is arranged in the housing and in which a lipid having lipophilic and hydrophilic groups is immobilized on a support disposed at the body fluid flow path, wherein body fluid components are separated from a body fluid utilizing the difference in adherence of the body fluid components to the hydrophilic groups of the lipid.

DESCRIPTION OF THE PREFERRED EMBODIMENTS

Figure 1:
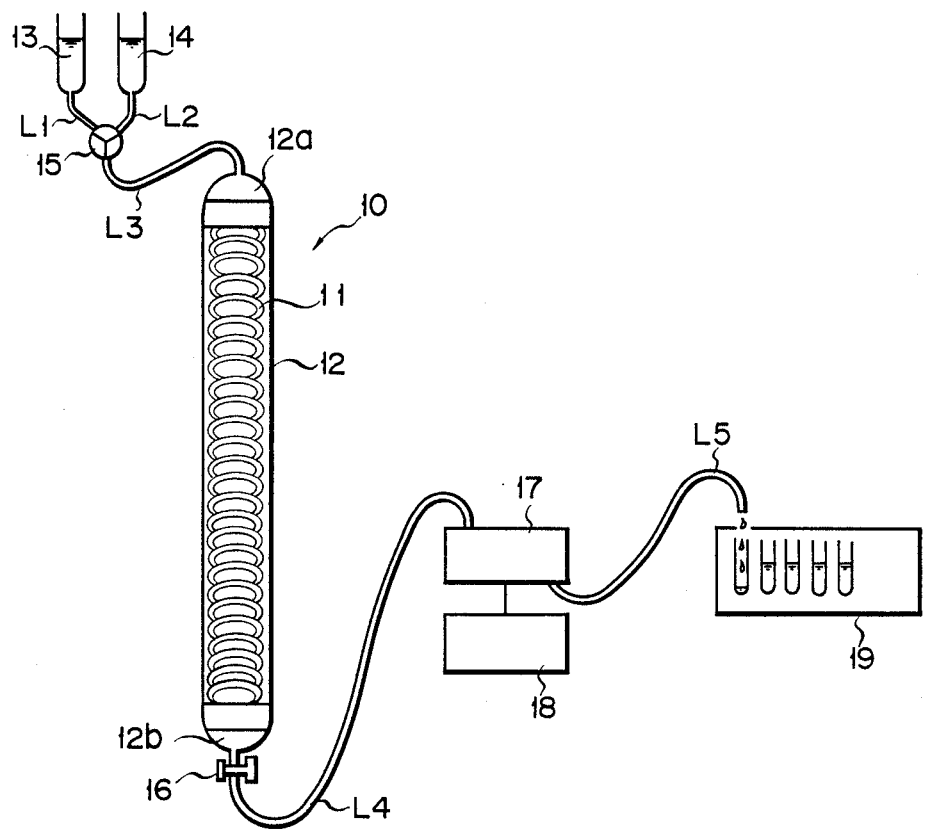
FIG. 1 is a diagram showing an example of a configuration of a body fluid component separation apparatus according to the present invention.

The present invention will now be described in detail.

The present invention is used for separating and recovering desired components from a body fluid such as lymph. As was mentioned earlier, although the present invention will be described with reference to separation and recovery of T- and B-cells as subsets of lymphocytes, the present invention is not limited to this particular application. Therefore, the present invention is applicable to separation of cells such as platelets or blood cells. To be more specific, the present invention can be applied to separation of any cell component of body fluids if it has an adherence to a specific type of group of a separation medium used different from remaining cell components.

According to the basic principle of the present invention, T- and B-cells as subsets of lymphocytes are separated and recovered utilizing the difference in adherence to a specific type of group of a separation medium, so that the recovered cells can be utilized for diagnosis and therapy. Although conventional methods of separating cells utilizing a difference in adherence to a specific substance are known, they do not provide satisfactory results, as described above.

According to the present invention, an amphiphilic lipid having both lipophilic and hydrophilic groups is used as a separation medium. However, if components to be separated are brought into contact with lipophilic groups, the adherence of these components to the lipophilic groups is too strong and does now allow easy removal. Even if the components can be removed, the functions of the components are impaired and normal testing or diagnosis cannot then be performed. In view of this fact, if the components of a body fluid to be separated are brought into contact with only the hydrophilic components of the lipid, the adherence between the component to be separated and the groups is appropriate. Separation of T- and B-cells does not result in impairment of cell functions and is easy to accomplish. The present invention has been established based upon this finding.

The separation medium to be used in the present invention is not limited to lipids but can be liposome formed of such a lipid. A separation medium wherein hydrophilic components and body fluid components to be separated can be brought into contact with each other is very much like a biomembrane and has an excellent biological compatibility. For this reason, the separation medium does not stimulate or cause damage to the cells and allows appropriate separation of cells in accordance with a difference in adherence to a specific substance and also allows easy peeling of cells adhering to such substance. Incidentally, the fact that the separation device of the present invention uses a lipid having both lipophilic and hydrophilic groups can be confirmed by a thin layer chromatography.

An adherent property of body fluid components to the lipid involves electrical attraction, physical coupling and other factors, and all such factors are represented by adherence according to the present invention.

A lipid or liposome must be supported or immobilized on a support or a substrate such that substantially only the hydrophilic groups can be brought into contact with body fluid components to be separated. (The term "substantially only the hydrophilic groups" is intended to include a case where only a very slight amount of the lipophilic groups may happen to contact the body fluid due to variations in manufacturing conditions of a separation device of the invention.) An immobilizing method and immobilizing agent therefor will be described in detail below. In a separation device of the present invention, a lipid or liposome constituted by such a lipid is immobilized such that its hydrophilic groups can be brought into contact with a body fluid. A separation apparatus of the present invention includes such a separation device assembled in a suitable apparatus.

Although an example of a separation means in which a lipid in the form of liposome is immobilized will be described below, the present invention is not limited to this.

(1) Separation means in which liposome is immobilized by hydrogel (1-1) Preparation of liposome Liposome is a closed cell consisting mainly of a phospholipid and has an aqueous medium incorporated therein. Examples of phospholipids may include phosphatidyl choline, phosphatidyl ethanolamine, phosphatidic acid, phosphatidyl serine, phosphatidyl inositol, phosphatidyl glycerol, sphingomyelin, and cardiolipin, and mixtures of two or more thereof. The liposome-forming material may contain, in addition to such a phospholipid, cholesterol as a component for reinforcing a liposome membrane structure. The liposome-forming material may also contain $\alpha$-tocopherol, ascorbic palmitate, or ascorbyl stearate as an antioxidant. The liposome-forming material may further contain dicetyl phosphate, diacetyl phosphate, or stearylamine as an agent for imparting electric charges to the liposome. The charged liposomes electrostatically repel to each other and do not coagulate with each other. If such additives are to be used, the membrane-reinforcing agent is contained in the amount of 20 to 50 mol %, the antioxidant is contained in the amount of 0.1 to 30 mol %, and the charging agent is contained in the amount of up to 15 mol % (per mole of all the liposome-forming material in each case).

The liposome-forming material containing the above components is suspended in a physiologically acceptable buffer solution such as a Tyrode's buffer or a Hank's balanced salt solution having a pH of 7.2 to 7.4 by a known method and is subjected to an ultrasonic treatment as needed. In this manner, a dispersion of liposome in the buffer solution is prepared. In order to remove free lipid, the dispersion is subjected to ultracentrifugation and only precipitated liposome is collected. If required, sizing is performed by means of a nuclipore membrane or the like. The final lipid content of the liposome in the dispersion is preferably 5 to 20 μmol/ml.

(1-2) Preparation of liposome/hydrogel

The above liposome is fixed by hydrogel. The hydrogel is a gel embracing water and is obtained by cooling a warm aqueous solution of a polymer or by polymerizing and crosslinking a monomer in an aqueous solution with radiation such as γ-rays with or without addition of a crosslinking agent. Original solutions of the hydrogel for the former type may include aqueous solutions of polyvinyl alcohol (e.g., 7.5 w/v % concentration), gelatin (e.g., 15 w/v % concentration), polyvinyl pyrrolidone (e.g., 20 w/v % concentration), poly(2-hydroxyethyl methacrylate), polymethacrylate, poly(N,N-dimethylaminoethyl methacrylate), polyethylene oxide, polysaccharide, sodium alginate, collagen, and fibrin. Original solutions for the hydrogel of the latter type may include an aqueous solution of acrylamide (e.g., 22.5 w/v % concentration). In either case, one of the buffer solutions as enumerated above is preferably used as a solvent. Methylenebisacrylamide can be used as a crosslinking agent to be added as needed, and is generally contained in the amount of 1 to 5% by weight.

The liposome dispersion is mixed with the hydrogel original solution preferably in a mixing ratio of 1:2 by volume, and the resultant solution is cooled or crosslinked. The dose of γ-rays for crosslinking is normally 1 to 5 Mrad. The aqueous solution of the polymer can be irradiated with γ-rays with or without the addition of the crosslinking agent. Upon exposure with γ-rays, a hydrogel having a crosslinked structure containing the liposome is obtained.

When the hydrogel original solution is an aqueous solution of acrylamide, irradiation with γ-rays can be replaced by addition of 5% tetraethylmethylenediamine and 2.5% potassium persulfate to the original solution each in the amount of 10%, and leaving the mixture to stand for 10 to 30 minutes.

The liposome has a bimolecular structure of lipids in which lipophilic groups of the lipids are directed to each other and hydrophilic groups of the lipids are directed to inner aqueous phase in the liposome or to the aqueous medium outside the liposome. Thus, only the hydrophilic groups contact the hydrogel molecules and therefore the body fluid.

(1-3) Support

The hydrogel incorporating the liposome is preferably immobilized on a suitable support. A hollow fiber is preferably used as such a support. Hollow fibers include porous hollow fibers of polypropylene, regenerated cellulose, polymethylmethacrylate, or an ethylene-vinyl acetate copolymer. The porous hollow fiber has a pore diameter of 2 nm to 0.4 μm and a porosity of 30 to 70%. A nonporous fiber can be used after being treated for allowing fixation of the hydrogel (e.g., treatment with a silane coupling agent). The support is not limited to a hollow fiber and can be a flat membrane, bead-like material or the like. The hydrogel incorporating the liposome can be supported on a porous carrier by entering into pores of the carrier.

(1-4) Preparation of separation device and apparatus

One to a hundred porous hollow fibers having a pore diameter of 20 Å to 0.4 μm, a length of 1 to 30 m, a porosity of 30 to 70%, and an inner diameter of 0.1 to 1 mm are bundled in a coil form. The two end portions of the coil are fixed with an epoxy resin or a polyurethane resin so that the open ends of each fiber are not closed, and the coil is placed in an acrylic resin tube or glass tube.

The liposome/hydrogel is passed through the inner spaces of the hollow fibers. After leaving the coil of hollow fibers to stand for 10 to 60 minutes, it is washed with the buffer solution. After the two end portions of the coil are covered with a parrafin film or the like to close the open ends of each fiber, the coil is irradiated with γ-rays at a dose of, for example, about 3 Mrad. Thereafter, any residual monomer or polymer is washed away with the buffer solution, and the obtained structure is used as a separation medium and a separation apparatus using it.

Although a description will be made below with reference to a case wherein a lipid is immobilized with a silane coupling agent, the present invention is not limited to this.

(2) Separation Means Immobilizing a Lipid With a Silane Coupling Agent

(2-1) Silane Coupling Agent and Its Coupling

Examples of the silane coupling agent may include octyltrimethoxysilane, octadecyltrimethoxysilane, N,N-dimethyl-N-octadecyl-3-aminopropyltrimethoxysilylchloride, and the like.

For example, 1% aqueous solution of N,N-dimethyl-N-octadecyl-3-aminopropyltrimethoxysilylchloride is placed in the inner space of glass capillaries or poured on glass beads in a plastic cup. After allowing to stand for 10 minutes, the solution is discarded. The treated capillaries or the beads are air-dried, and subjected to curing at 110° C. for 1 hour.

(2-2) Lipid and Adsorption Thereby

One or more of phospholipids such as phosphatidyl choline, phosphatidyl ethanolamine, phosphatidic acid, phosphatidyl serine, phosphatidyl inositol, phosphatidyl glycerol, sphingomyelin, and cardiolipin are preferably used as lipid(s).

For example, 35 to 100 mol % of phosphatidyl choline and, if a charge is to be imparted, 0 to 15 mol % of dicetyl phosphate, diacetyl phosphate or stearylamine are dissolved in chloroform to prepare a chloroform solution. The lipid content in the chloroform solution is preferably 5 to 20 μmol/ml.

The solution is filled in the inner spaces of the glass capillaries or glass beads in the plastic cup and subjected to the treatment described in item (2-1) above. After leaving the solution to stand for one hour, the solution is drained and the hollow fiber or cup is lightly washed with distilled water. The hollow fiber or cup is dried under a reduced pressure and is thereafter used as a separation medium.

(2-3) Preparation of Separation Apparatus

One to a hundred glass capillaries having a length of 1 to 30 m and subjected to the treatment as in item (2-2) above are bundled in a coil. After the two end portions of the coil are fixed with an epoxy resin or an urethane resin, the coil is placed in an acrylic resin or glass tube. Alternatively, glass beads subjected to the treatment in item (2-2) above are filled in an acrylic resin column or glass column having a nylon net or a stainless mesh mounted at the bottom.

The lipids form a lipophilic bond with the carbon chain of the silane coupling agent. The lipophilic groups of the lipids involve the bond with the silane coupling agent, and the hydrophilic groups of the lipids are free and contact the body fluid.

An embodiment of a body fluid component separation apparatus according to the present invention will be described with reference to FIG. 1. A separation apparatus shown in FIG. 1 has a column 12 housing a coil separation device 11 having the above-mentioned structure. A body fluid inlet port 12a of the column 12 is connected to a body fluid container 13 and a buffer solution container 14 through a three-way cock 15. The containers 13 and 14 and the cock 15 are connected through lines L1 and L2, and the inlet port 12a and the cock 15 are connected through a single line L3. The outlet port 12b of the column 12 is connected to a turbidity detector 17 using a flow cell through a line L4 with a cock 16 mounted midway therealong. The detector 17 is connected to a turbidity recorder 18. A line L5 for flowing an output body fluid fraction is connected to the detector 17. The fraction flowing through the line L5 is collected by a fraction collector 19 consisting of a plurality of test tubes.

In operation, a suspension of a leucocyte fraction in a buffer solution at a concentration of $10^6$ to $10^7$ leucocytes/ml is prepared. The leucocyte fraction is prepared by separation, using a sodium metholizoatephicol solution mixture (1.077 specific weight at 20° C.) from heparin-added human peripheral blood, by the specific weight centrifugation method and washing the obtained fraction with a buffer solution.

The suspension is poured into the container 13 of the separation apparatus 10. After the cock 15 is adjusted to allow the suspension in the container 13 to slowly flow into the separation device 11 in the column 12 (i.e., into the inner spaces in the hollow fibers or glass capillaries), the buffer solution held in the container 14 is continuously flowed. Any of the above-mentioned separation devices can be used as the device 11 in the column 12. The turbidity of the output solution is detected by the detector 17. Each predetermined amount of output fraction is collected in the collector 19 while monitoring a peak recorded by the recorder 18, thereby recovering cells.

A description will be made with reference to an example wherein liposome is immobilized on a support of porous hollow fibers with hydrogel.

Figure 2A:
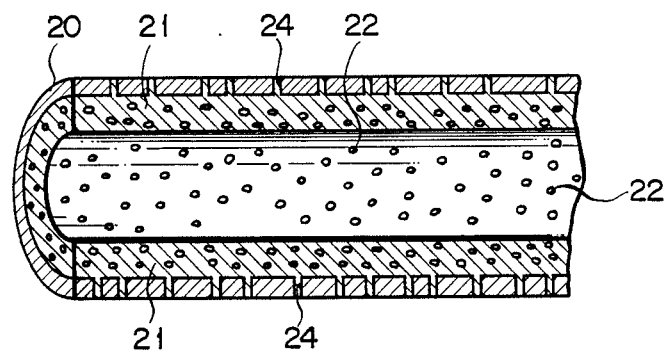
FIG. 2A is a sectional view of a separation device in which liposome is immobilized to a porous hollow fiber with hydrogel.
Figure 2B:
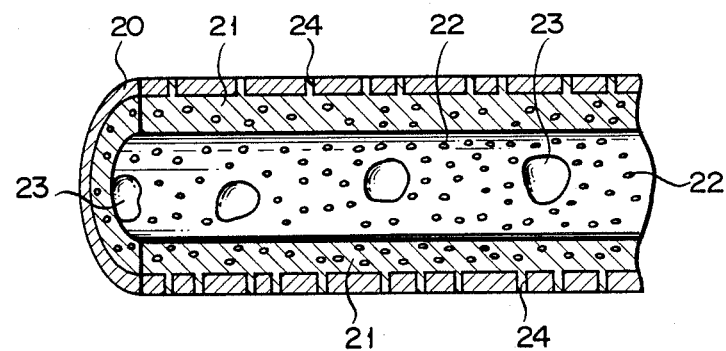
FIG. 2B is a sectional view showing a state wherein B-cells of lymphocytes are adhered when lymphocytes are passed through the separation device shown in FIG. 2A.

An example of this separation device is shown in FIG. 2. As shown in FIG. 2A, hydrogel 21 is fixed in a number of pores 24 in a hollow fiber 20, and liposome 22 indicated by small hollow dots is fixed inside the hollow fiber 20 with the hydrogel 21. In this state, in the liposome formed by a plurality of lipids, the lipophilic groups of lipids are aligned inside and the hydrophilic groups are aligned at the outside such that the hydrophilic groups are exposed to the hollow portion of the fiber, i.e., the path of the body fluid. This is emphasized with small dots indicated by reference numeral 22 in FIG. 2A.

When the body fluid is flowed in each hollow fiber in the separation/collecting operation described above, as indicated in FIG. 2B, B-cells 23 as a subset of the lymphocytes are adhered to the liposome 22. However, since T-cells have a small adherence to the liposome as compared to the B-cells, they are left to flow through the hollow portion inside the fiber. Therefore, initially, the detector 17 detects only T-cells and only T-cells are collected. The B-cells adhering to the liposome can be removed therefrom by a solution such as the buffer solution, thereby allowing recovery of only B-cells.

An example will now be described wherein a lipid is immobilized on a glass capillary support with a silane coupling agent.

In this example, referring to FIG. 2, reference numeral 20 denotes a glass capillary 24 with no pores; 21, a silane coupling agent; and 22, a lipid. Then, adherence of B-cells 23 of lymphocytes to the lipid can be explained by the same description given above.

B-cells as a subset of lymphocytes are adhered to and trapped by the hydrophilic groups of a lipid or liposome for more than one reason. B-cells have an uneven surface compared to T-cells when observed through an electron microscope. Therefore, when B-cells are entangled with lipophilic groups of the lipid or liposome or nylon fibers, the adherence becomes too strong and does not allow easy separation. Adherence of the B-cells to the hydrophilic groups of the lipid or liposome has a sufficient difference from that of T-cells, and at the same time allows easy removal to be performed later.

The adherence of B-cells to the hydrophilic groups of the lipid or liposome is also considered to be attributable to electrical attraction. In this manner, adherent property of B-cells to the hydrophilic groups of the lipid or liposome is considered to be attributable to physical and electrical coupling.

According to the present invention, an excellent separation medium, apparatus and method can be obtained by selectively combining a support and a substance having a cell separation function.

A particularly excellent effect is obtained with a combination of the porous hollow fiber, hydrogel and liposome or with a combination of the glass capillary (or glass beads), the silane coupling agent, and the lipid. Either combination allows reliable and simple immobilization of liposome or lipid on the carrier. The hydrophilic groups of the lipid or liposome are aligned along the body fluid flow path, while the lipophilic groups are not, thereby providing excellent separation performance.

Regarding the separation performance of B- and T-cells by the lipid or liposome, since the B-cells have a strong adherent property to the hydrophilic groups while the T-cells have a weak adherent property, and the difference in adherence is of appropriate degree, the B- and T-cells are reliably separated and recovered. Removal of the B-cells adhering to the hydrophilic groups of the lipid or liposome can be easily performed by, for example, flowing the buffer solution. Thus, the desired type of cells can be recovered without impairing functions of the recovered cells.

In the manufacture of a separation apparatus using the separation device comprising a combination as described above, only simple procedures such as flowing a body fluid and a buffer solution are required, and a special device is not required unlike in the conventional methods.

According to the present invention, since B- and T-cells can be separated and recovered without impairing the function of these cells, the recovered cells can be used not only for clinical tests but also for therapy of immunological diseases or culture of cells.

The present invention will now be described by way of its Examples.

EXAMPLE 1

Liposomes of compositions (a) and (b) below were prepared following the procedures given in item (1-1) above:

| | Liposome Component Molar Ratio | | | | |
|---|---|---|---|---|---|
| | EPC | SPM | Chol | VE | DCP |
| (a) | 8 | 2 | 10 | 0.3 | — |
| (b) | 8 | 2 | 10 | 0.3 | 1 |

Lipid Concentration: 18.3 μmol/ml
EPC: Egg-yolk phosphatidyl choline
SPM: Sphingomyelin
Chol: Cholesterol
VE: α-Tocopherol
DCP: Dicetylphosphate The liposome was mixed with a hydrogel original solution containing 7.5 w/v % polyvinyl alcohol (polymerization degree: about 2,000) and 1.5 w/v % N,N-methylenebisacrylamide in the buffer solution. After wetting the inner surface of polypropylene hollow fibers having a pore diameter of 0.55 μm and a porosity of 45%, the obtained liposome/hydrogel original solution was coated on the inner surface of the porous hollow fibers and irradiated with γ-rays at a dose of 3 Mrad to effect polymerization and crosslinking, obtaining the separation device.

Figure 3:
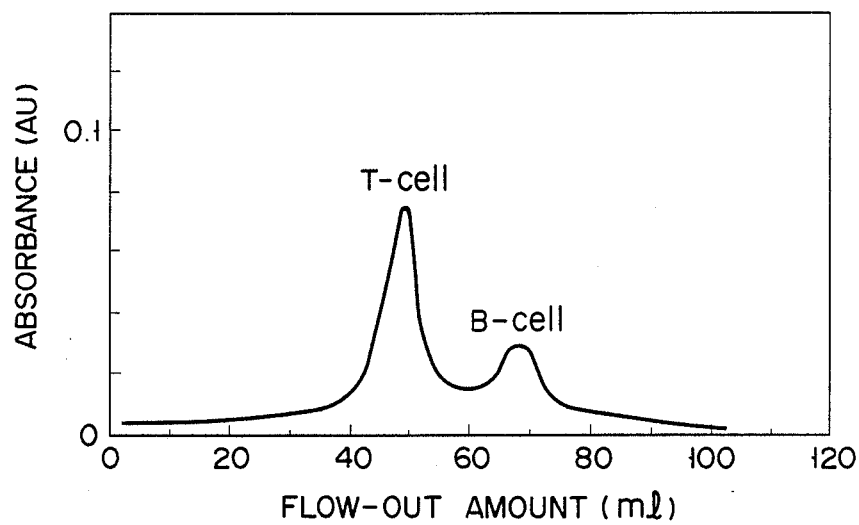
FIG. 3 is a chromatogram obtained when lymphocytes are separated using a separation device obtained by coating a liposome/hydrogel solution on the inner surface of a hollow fiber.

The separation device thus obtained was set in the apparatus as shown in FIG. 1, cell separation and recovery was performed in a manner to be described later, and the cell separation state was observed. The results obtained with the composition (b) are shown in the graph in FIG. 3.

Substantially the same results as that with the composition (b) were obtained with the composition (a).

A suspension ($5 \times 10^6$ cells/ml) of lymphocytes sampled from normal peripheral human blood was flowed into the column, and the buffer solution was flowed thereafter. The turbidity (absorbance) of the solution flowing out of the column was continuously measured and recorded at a wavelength of 400 nm. The solution was sampled in fractions of 2.5 ml with a fraction collector (rectangular weight-type fraction collector SF-160Z available from Toyo Seisakusho K.K.), and cells were recovered.

EXAMPLE 2

A lipid of the composition given below was immobilized on the inner surface of a glass capillary of 25 m length with 1% N,N-dimethyl-N-octadecyl-3-aminopropyltrimethoxysilylchloride in the manner described in item (2-2) above, and a separation device was thus obtained.

The separation device was set in the apparatus shown in FIG. 1, and cell separation was performed following the same procedures as in Example 1.

| Component | Molar ratio | |
|---|---|---|
| | EPC | SA |
| (c) | 10 | — |
| (d) | 10 | 1.2 |

Figure 4:
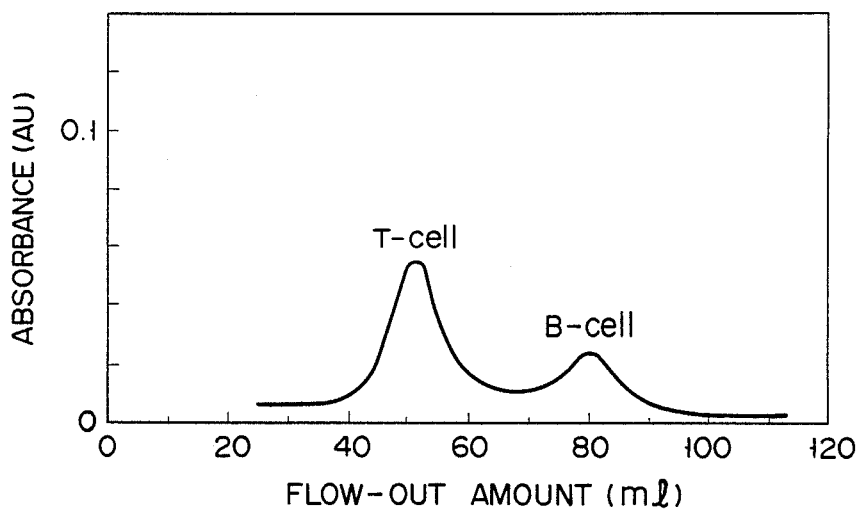
FIG. 4 is a chromatogram obtained when lymphocytes are separated using a separation device obtained by coating a silane coupling agent on the inner surface of a glass capillary.

Lipid content: 10 μmol/ml-CHCl3
EPC: Egg-yolk phosphatidyl choline
SA: Stearylamine The results obtained with the composition (d) are shown in the graph in FIG. 4. Substantially the same results were obtained with the composition (c).

What is claimed is:

1. A method of separating a body fluid into respective components thereof, comprising the steps of:
providing a separator comprising at least one hollow fiber defining a body fluid flow path therein, said at least one hollow fiber being porous and containing at least one lipid having lipophilic groups and hydrophilic groups, and an immobilizer comprising hydrogel on an inner surface of said hollow fiber, said hydrogel having a crosslinked structure permeating into the pores of the porous hollow fiber whereby it is bonded to the porous fiber and immobilizing said at least one lipid such that the hydrophilic groups are directed towards said body fluid flow path;
flowing the body fluid through said body fluid flow path, whereby said body fluid contacts substantially only said hydrophilic groups of said lipid whereby a component of said contacted body fluid which has a strong adherent property to said hydrophilic groups adhers to said hydrophilic groups; and
collecting the residue of said body fluid, thereby separating from said body fluid said component having the strong adherent property to the hydrophilic groups.

2. A method according to claim 1, wherein the lipid is a phospholipid.

3. A method according to claim 2, wherein the phospholipid is at least one member selected from the group consisting of phosphatidyl choline, phosphatidyl ethanolamine, phosphatidic acid, phosphatidyl serine, phosphatidyl inositol, phosphatidyl glycerol, sphingomyelin, and cardiolipin.

4. A method according to claim 2, wherein the phospholipid is in the form of liposome.

5. A method according to claim 1, wherein the hydrogel is supported on an inner surface of a porous hollow fiber.

6. A method according to claim 1, wherein the body fluid contains lymphocytes, and the component having the strong adherent property to the hydrophilic groups is B-cells.

7. A method according to claim 6, wherein the body fluid comprises a suspension of lymphocytes sampled from peripheral human blood.

8. A method according to claim 6, wherein the body fluid comprises lymph.

9. A method according to claim 1, wherein said hydrogel is selected from the group consisting of polyvinyl alcohol, gelatin, polyvinyl pyrrolidone, poly (2-hydroxyethyl methacrylate), polymethacrylate, poly (N,N-dimethylaminoethyl methacrylate), polyethylene oxide, polysaccharide, sodium alginate, collagen, fibrin, and polyacrylamide.

10. The method of claim 1 wherein said lipid is in the form of a liposome.

* * * * *